United States Patent
Jing

(10) Patent No.: US 10,750,993 B2
(45) Date of Patent: Aug. 25, 2020

(54) TONGUE MANIFESTATION DETECTING DEVICE AND TONGUE MANIFESTATION DETECTING APPARATUS COMPRISING THE SAME

(71) Applicants: BOE Technology Group Co., Ltd., Beijing (CN); HEFEI BOE OPTOELECTRONICS TECHNOLOGY CO., LTD., Hefei, Anhui (CN)

(72) Inventor: Yangkun Jing, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 458 days.

(21) Appl. No.: 15/688,919

(22) Filed: Aug. 29, 2017

(65) Prior Publication Data

US 2018/0116585 A1 May 3, 2018

(30) Foreign Application Priority Data

Oct. 28, 2016 (CN) .......................... 2016 1 0972675

(51) Int. Cl.
*A61B 5/00* (2006.01)
(52) U.S. Cl.
CPC .......... *A61B 5/4542* (2013.01); *A61B 5/0035* (2013.01); *A61B 5/0075* (2013.01); *A61B 5/0088* (2013.01); *A61B 2560/04* (2013.01)

(58) Field of Classification Search
CPC ... A61B 5/0075; A61B 5/0077; A61B 5/4542; A61B 5/4552; A61B 5/01; A61B 5/4854
See application file for complete search history.

(56) References Cited

U.S. PATENT DOCUMENTS

| | | | |
|---|---|---|---|
| 2008/0090198 A1* | 4/2008 | Liang | A61B 5/0066 433/29 |
| 2009/0179986 A1* | 7/2009 | Klett | A61B 5/1114 348/77 |
| 2011/0299034 A1* | 12/2011 | Walsh | A61B 3/0091 351/206 |
| 2012/0271180 A1* | 10/2012 | Ren | A61B 5/02055 600/500 |
| 2014/0152970 A1* | 6/2014 | Wada | A61B 5/1076 356/3 |

(Continued)

FOREIGN PATENT DOCUMENTS

CN 105342566 A * 2/2016

*Primary Examiner* — Bill Thomson
*Assistant Examiner* — Aminah Asghar
(74) *Attorney, Agent, or Firm* — Nath, Goldberg & Meyer; Joshua B. Goldberg

(57) ABSTRACT

The present discourse provides a tongue manifestation detecting device. The tongue manifestation detecting device comprises: an image acquisition component configured to acquire a surface image of a tongue; a temperature acquisition component configured to acquire parameters characterized by the temperature of the tongue; and a brightness temperature image generation component configured to generate a brightness temperature image of the tongue based on the parameters characterized by the temperature of the tongue acquired by the temperature acquisition component.

17 Claims, 1 Drawing Sheet

(56) References Cited

U.S. PATENT DOCUMENTS

2016/0206204 A1\* 7/2016 Matsuda .............. A61B 5/0077
2016/0249811 A1\* 9/2016 Khan ................. A61B 1/00009
                                                        600/474
2017/0000432 A1\* 1/2017 Lim ........................ A61B 6/10

\* cited by examiner

TONGUE MANIFESTATION DETECTING DEVICE AND TONGUE MANIFESTATION DETECTING APPARATUS COMPRISING THE SAME

CROSS-REFERENCE TO RELATED APPLICATION

This application claims priority to Chinese Patent Application No. 201610972675.1, filed on Oct. 28, 2016 in the Chinese Intellectual Property Office, the disclosure of which is incorporated herein by reference.

FIELD OF THE INVENTION

The present disclosure relates to the field of medical apparatus and instruments, and more specifically relates to a tongue manifestation detecting device and a tongue manifestation detecting apparatus comprising the same.

BACKGROUND OF THE INVENTION

An important method of Chinese medicine diagnosis is to observe a subject's tongue, through which to determine whether the subject falls ill and what kind of the illness.

Generally, a doctor observes the subject's tongue with his/her naked eyes, and then judges the subject's tongue manifestation. However, this method of observing tongue with the naked eyes causes less accurate, and can't fully obtain a variety of parameters of tongue manifestation.

SUMMARY OF THE INVENTION

In order to solve at least one of the above problems, the present disclosure provides a tongue manifestation detecting device comprising an image acquisition component configured to acquire a surface image of a tongue, a temperature acquisition component configured to acquire parameters characterized by the temperature of the tongue, and a brightness temperature image generation component configured to generate a brightness temperature image of the tongue based on the parameters characterized by the temperature of the tongue acquired by the temperature acquisition component.

According to an embodiment of the present disclosure, the parameter characterized by the temperature of the tongue comprises an intensity of the infrared emitted from the tongue. The temperature acquisition component is capable of acquiring an intensity value of the infrared emitted from the tongue. The brightness temperature image generation component is capable of generating the brightness temperature image of the tongue based on the intensity value of the infrared acquired by the temperature acquisition component.

According to an embodiment of the present disclosure, the temperature acquisition component stores an initial standard infrared intensity value, and is capable of calculating the intensity value of the infrared emitted from the tongue according to the following formula:

$$If_i = If_r - If_s;$$

where $If_i$ represents the intensity value of the infrared emitted from the tongue, $If_r$ represents an intensity value of the received infrared, and $If_s$ represents the initial standard infrared intensity value.

According to an embodiment of the present disclosure, the tongue manifestation detecting device further comprises an infrared light source configured to emit infrared to the tongue. The temperature acquisition component is configured to receive infrared from the tongue and is capable of calculating the intensity of the infrared emitted from the tongue based on the intensity of the infrared emitted from the infrared light source and the intensity of the infrared received from the tongue.

According to an embodiment of the present disclosure, the infrared light source comprises a plurality of infrared light-emitting diodes arranged in an array form.

According to an embodiment of the present disclosure, the plurality of infrared light-emitting diodes are capable of emitting infrared with different wavelengths alternately. The temperature acquisition component is capable of acquiring the intensity of the infrared reflected by the tongue when irradiated by the infrared of various wavelengths. The brightness temperature image generation component is capable of generating a plurality of brightness temperature images of the tongue based on the infrared intensity, corresponding to the plurality of the infrared light-emitting diodes, acquired by the temperature acquisition component.

According to an embodiment of the present disclosure, the image acquisition component comprises a light source, a spectroscope, a filter lens, a controllable lens and an imaging component. The focal length of the controllable lens can be adjusted. The imaging component is provided in the reflected light path of the spectroscope, and is capable of generating the surface image of the tongue. The light source, the spectroscope, the filter lens and the controllable lens are arranged in the same straight line in this order, and the imaging component and the spectroscope are arranged in another straight line. The straight line where the imaging component and the spectroscope are located is perpendicular to the straight line where the light source, the spectroscope, the filter lens and the controllable lens are located.

According to an embodiment of the present disclosure, the image acquisition component further comprises an image delayer and a controllable grating both located between the imaging component and the spectroscope. The imaging component comprises an image sensor and a mirror. The mirror, the image delayer, the controllable grating and the spectroscope are arranged in the same straight line in this order. The reflecting surface of the mirror faces a light outlet of the image delayer, and there is an angle between the reflecting surface of the mirror and the straight line where the mirror, the image delayer, the controllable grating and the spectroscope are located. The light passing through the image delayer is reflected by the mirror to the image sensor.

In the tongue manifestation detecting device provided in the present disclosure, a surface image of the tongue may be acquired by the image acquisition component. The surface image of the tongue comprises an upper surface image and/or a lower surface image of the tongue. The doctor can judge the surface state of the tongue of the subject according to the image acquired by the image acquisition component without using the naked eye to observe the tongue of the subject directly, which is more convenient and avoids the influence of the doctor's naked eye on the observation effect.

In a case where the surface image of the tongue comprises the upper surface image of the tongue, the doctor can obtain the state of the coated tongue of the subject. In a case where the surface image of the tongue comprises the lower surface image of the tongue, the doctor can obtain the state of the lingual vein of the subject.

The temperature of the various parts of the tongue may be estimated by the brightness temperature image generation component, so as to provide doctors with more parameters of the tongue manifestation, which is conducive for doctors to diagnose and treat the subject.

According to an embodiment of the present disclosure, the present disclosure also provides a tongue manifestation detecting apparatus comprising the above-described tongue manifestation detecting device including the image acquisition component, the temperature acquisition component and the brightness temperature image generation component. The tongue manifestation detecting apparatus further comprises a mounting bracket comprising a support portion, a mounting portion and a connector. The connector is connected to the mounting portion at one end and is connected to the support portion at the other end such that the mounting portion is located on just one side of the support portion. The image acquisition component and the temperature acquisition component are provided on the two end of the mounting portion, respectively. The mounting portion is capable of rotating around the connector to exchange the relative positions of the image acquisition component and the temperature acquisition component.

According to an embodiment of the present disclosure, at least one of the image acquisition component and the temperature acquisition component is capable of moving on the mounting portion such that the distance between the image acquisition component and the temperature acquisition component may be changed, e.g. increased or reduced.

According to an embodiment of the present disclosure, the mounting portion is a curved beam, the opening of the mounting portion faces away from the support portion, and one end of the connector is connected to a middle portion of the mounting portion.

According to an embodiment of the present disclosure, the support portion extends in a predetermined direction, and the connector can be reciprocally moved in the predetermined direction of the support portion to drive the mounting portion to reciprocate in the predetermined direction of the support portion.

According to an embodiment of the present disclosure, the tongue manifestation detecting apparatus further comprises a base on which the mounting bracket is fixed.

BRIEF DESCRIPTION OF THE DRAWINGS

The accompanying drawings constituting a part of the specification are intended to provide a further understanding of the present disclosure and explain the disclosure together with the following preferred embodiments, but should not be considered as limiting the scope of the disclosure. In the drawings.

DESCRIPTION OF THE PREFERRED EMBODIMENT

Hereinafter, preferred embodiments of the present disclosure will be described in detail with reference to the accompanying drawings. It is to be understood that the preferred embodiments described herein are for the purpose of illustration and explanation only and are not intended to limit the present disclosure.

Figure 1:
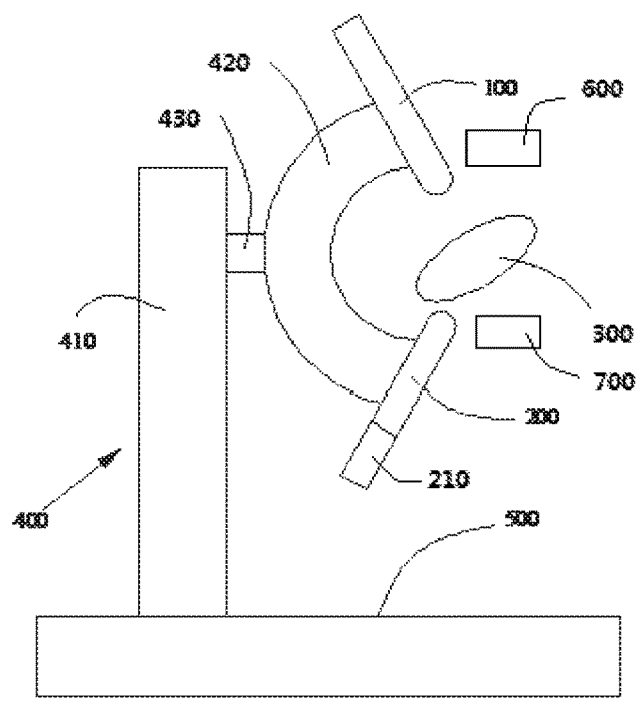
FIG. 1 is a schematic structural diagram of a tongue manifestation detecting apparatus according to the present disclosure.

As shown in FIG. 1, the present disclosure provides a tongue manifestation detecting device. The tongue manifestation detecting device comprises: an image acquisition component 100 configured to acquire a surface image of a tongue 300; a temperature acquisition component 200 configured to acquire parameters characterized by the temperature of the tongue 300; and a brightness temperature image generation component 210 connected to the temperature acquisition component 200. The brightness temperature image generation component 210 is configured to generate a brightness temperature image of the tongue 300 based on the parameters characterized by the temperature of the tongue 300 acquired by the temperature acquisition component 200.

The temperature of the various parts of the tongue 300 may be estimated by the brightness temperature image generation component 210, so as to provide doctors with more parameters of the tongue manifestation, which is conducive for doctors to diagnose and treat the subject.

According to an embodiment of the present disclosure, the tongue manifestation detecting device may further comprise a master device, in which the brightness temperature image generation component 210 may be integrated. The master device may comprise a USB interface drive module, an image capture module, an image processing module and an image management module. The image capture module is configured to capture the surface image of the tongue acquired by the image acquisition component 100 and the brightness temperature image of the tongue generated by the brightness temperature image generation component 210. The image acquisition component 100 and the temperature acquisition component 200 are connected to the master device via the USB interface drive module so as to transmit the surface image to the image capture module and transmit the parameters characterized by the temperature of the tongue to the brightness temperature image generation component 210. The image processing module is configured to process the image captured by image capture module.

In the present disclosure, there is no particular requirement for parameters characterized by the temperature of the tongue. For example, the parameters that characterized by the temperature of the tongue can be directly the temperature of the tongue, or the intensity of the infrared emitted from the tongue.

According to an embodiment of the present disclosure, in a case where the temperature parameter of the tongue comprises the intensity of the infrared emitted from the tongue, temperature acquisition component 200 may acquire the intensity values of the infrared reflected at different positions of the tongue, and brightness temperature image generation component 210 can puzzle the intensity values at different positions so as to generate the brightness temperature image of the tongue in which different colors may represent different intensity values.

In the present disclosure, there is no particular requirement on how to acquire the intensity value of the infrared. For example, the infrared intensity of the tongue can be detected directly. Specifically, the temperature acquisition component 200 stores an initial standard infrared intensity value, and may subtract the initial standard infrared intensity value from an intensity value of the received infrared so as to obtain an intensity value of the infrared emitted from the tongue.

Specifically, the intensity value of the infrared emitted from the tongue may be calculated according to the following formula:

$$If_t = If_r - If_s;$$

where $If_i$ represents the intensity value of the infrared emitted from the tongue, $If_r$ represents the intensity value of the received infrared, and $If_s$ represents the initial standard infrared intensity value.

In such an embodiment, the temperature acquisition component 200 may be an infrared sensor chip.

The initial standard infrared intensity value represents the infrared intensity value existed in the environment, which is related to ambient temperature. The ambient temperature can be measured in advance before the tongue manifestation is detected by the tongue manifestation detecting device, and then the ambient temperature is converted into the corresponding infrared intensity value. The infrared intensity acquired by the temperature acquisition component 200 comprises the infrared intensity of the tongue and the infrared intensity in the environment. The temperature acquisition component 200 subtracts the initial standard infrared intensity value from the intensity value of the received infrared to obtain the intensity value of the infrared emitted from the tongue.

As another embodiment of the present disclosure, the tongue manifestation detecting device further comprises infrared light sources 600 and 700. As shown in FIG. 1, the infrared light sources 600 and 700 are provided above and below the tongue, respectively. The infrared light source 600 and 700 are configured to emit infrared towards the tongue, the temperature acquisition component 200 is configured to receive infrared from the tongue, and to calculate the intensity of the infrared emitted from the tongue based on the intensity of the infrared emitted from the infrared light source and the intensity of the infrared reflected by the tongue. The infrared light source 600 is turned on when the upper surface of the tongue is detected, and the infrared light source 700 is turned on when the lower surface of the tongue is detected.

The tongue itself emits infrared, so the infrared from the tongue consists of two parts: one is the infrared emitted from the tongue and the other is the infrared reflected by the tongue when irradiated by the infrared light source. The temperature acquisition component 200 obtains the intensity of the infrared emitted from the tongue by subtracting the intensity of the infrared reflected by the tongue (substantially equal to the intensity of the infrared emitted from the infrared light source) from the intensity of the received infrared.

In the present disclosure, there is no particular requirement for the specific structure of the infrared light source. For example, the infrared light source may comprise a plurality of infrared light-emitting diodes arranged in an array form. The infrared emitted from the infrared light source may irradiate the surface of the entire tongue such that the temperature of the tongue surface may be completely acquired.

As another embodiment of the present disclosure, the plurality of infrared light-emitting diodes are capable of emitting infrared with different wavelengths alternately. The temperature acquisition component 200 is capable of acquiring the intensity of the infrared reflected by the tongue when irradiated by the infrared of various wavelengths, and the brightness temperature image generation component 210 is capable of generating a plurality of brightness temperature images of the tongue based on the infrared intensity, corresponding to the plurality of the infrared light-emitting diodes, acquired by the temperature acquisition component 200.

A number of different brightness temperature images may be generated under the irradiation of infrared of various wavelengths. The tongue has a different absorption rate for the infrared of different wavelengths. By irradiating the tongue with the infrared of various wavelengths, it is possible to find a wavelength that has the least effect on the absorption rate of the tongue, and thus the brightness temperature images obtained by irradiating the tongue with the infrared of the wavelength is the most clear and accurate.

In the tongue manifestation detecting device provided in the present disclosure, the surface image of the tongue may be acquired by the image acquisition component 100. The surface image of the tongue comprises an upper surface image and/or a lower surface image of the tongue. The doctor can judge the surface state of the tongue of the subject according to the image acquired by the image acquisition component 100 without using the naked eye to observe the tongue of the subject directly, which is more convenient and avoids the influence of the doctor's naked eye on the observation effect.

When the surface image of the tongue comprises the upper surface image of the tongue, the doctor can obtain the state of the coated tongue of the subject. When the surface image of the tongue comprises the lower surface image of the tongue, the doctor can obtain the state of the lingual vein of the subject.

Figure 2:
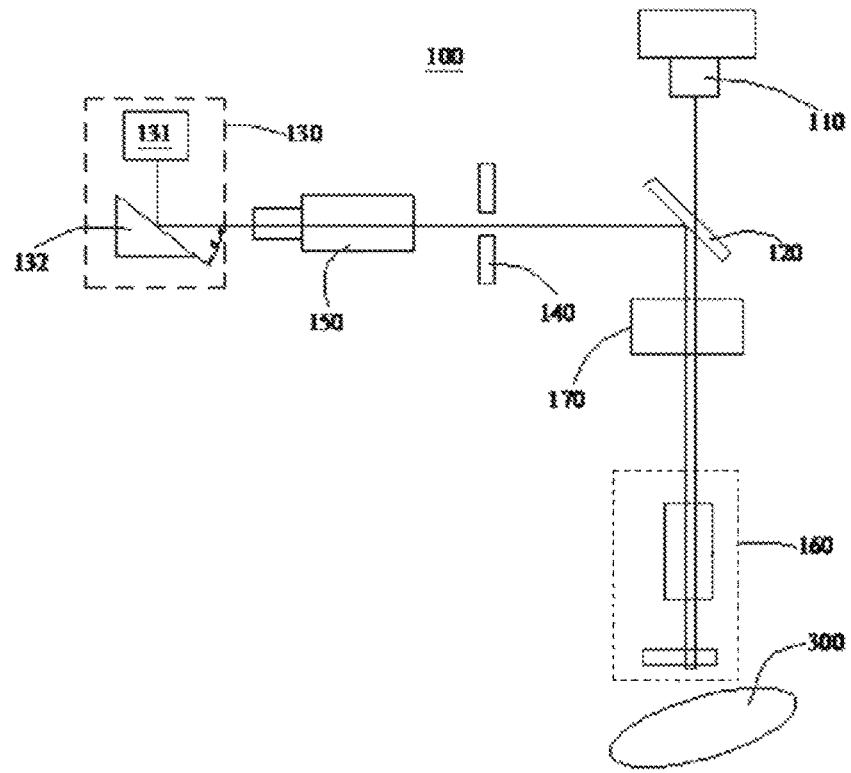
FIG. 2 is a schematic structural diagram of an image acquisition component.

In the present disclosure, there are no particular limits on the structure of the image acquisition component 100. For example, the image acquisition component 100 may comprise a light source 110, a spectroscope 120, a filter lens 170, a controllable lens 160 and an imaging component 130. As shown in FIG. 2, the spectroscope 120 is provided between the light source 110 and the filter lens 170. The light source 110, the spectroscope 120, the filter lens 170 and the controllable lens 160 are arranged in the same straight line in this order, and the focal length of the controllable lens 160 can be adjusted. The imaging component 130 is provided in the reflected light path which formed by reflecting the light from the tongue with the spectroscope 120, and is capable of generating the surface image of the tongue. The imaging component 130 and the spectroscope 120 are arranged in another straight line, and the straight line where the imaging component 130 and the spectroscope 120 are located is perpendicular to the straight line where the light source 110, the spectroscope 120, the filter lens 170 and the controllable lens 160 are located. The light source 110 is an infrared light source.

Specifically, the process of the image acquisition component 100 acquiring the original image of the surface of the tongue comprises two steps, namely, an irradiating step and a capturing step. The irradiating step is achieved by the light source 110, the spectroscope 120, the filter lens 170 and the controllable lens 160 together. The capturing step is achieved by the light source 110 and the imaging component 130 together. Specifically, the infrared light emitted from the light source 110 passes through the spectroscope 120 and is divided into two parts, a part of the light is reflected by the spectroscope 120, and the other part of the light passes through the spectroscope 120 to reach the controllable lens 160 and is irradiated on the tongue to be detected to achieve the irradiating step. The light irradiated on the surface of the tongue is reflected by the surface of the tongue to form an interference light having a specific wavelength, the interference light is irradiated on the spectroscope 120 and is reflected by the spectroscope 120 to the imaging component 130 so that the original image of the surface film of the tongue can be obtained to achieve the capturing step.

After the original image is obtained, the original image may be processed using a band-pass filter, through which the contrast ratio of the original image may be adjusted to obtain a more accurate tongue surface image.

Here, the controllable lens 160 refers to a lens in which the focal length is adjustable. The controllable lens 160 may comprise a retractable lens and a servo motor, and the retractable lens can be adjusted by the servo motor to adjust the focal length of the controllable lens 160. The filter lens 170 may filter out unwanted stray light to make the obtained image more accurate.

According to an embodiment of the present disclosure, the image acquisition component 100 further comprises an image delayer 150 and a controllable grating 140 both provided between the imaging component 130 and the spectroscope 120. Further, as shown in FIG. 2, the imaging component 130 comprises an image sensor 131 and a mirror 132. The mirror 132, the image delayer 150, the controllable grating 140 and the spectroscope 120 are arranged in the same straight line in this order. The reflecting surface of the mirror 132 faces a light outlet of the image delayer 150, and there is an angle a between the reflecting surface of the mirror 132 and the straight line where the mirror 132, the image delayer 150, the controllable grating 140 and the spectroscope 120 are located. The light passing through the image delayer 150 is reflected by the mirror 132 to the image sensor 131.

For ease of arrangement, preferably, the angle a between the reflecting surface of the mirror 132 and the straight line where the mirror 132, the image delayer 150, the controllable grating 140 and the spectroscope 120 are located is 45°.

As another embodiment of the present disclosure, the present disclosure also provides a tongue manifestation detecting apparatus comprising the tongue manifestation detecting device according to the disclosure. As shown in FIG. 1, the tongue manifestation detecting apparatus further comprises a mounting bracket 400 comprising a support portion 410, a mounting portion 420 and a connector 430. The connector 430 is connected to the mounting portion 420 at one end and is connected to the support portion 410 at the other end such that the mounting portion 420 is located on just one side (herein refers to the right side or the left side) of the support portion 410. The image acquisition component 100 and the temperature acquisition component 200 are provided on the two end of the mounting portion 420, respectively, and the mounting portion 420 may be rotated around the connector 430 to exchange the relative positions of the image acquisition component 100 and the temperature acquisition component 200.

In order to obtain a more comprehensive tongue manifestation parameter by using the tongue manifestation detecting apparatus, firstly, the upper surface image of the tongue 300 can be acquired by the image acquisition component 100, and the parameter characterized by the temperature of the lower surface of the tongue can be acquired by the temperature acquisition component 200 so that the brightness temperature image of the lower surface of the tongue 300 is generated by the brightness temperature image generation component 210. Thereafter, the mounting portion 420 is rotated, in this case, the parameter characterized by the temperature of the upper surface of the tongue 300 can be acquired by the temperature acquisition component 200 so that the brightness temperature image of the upper surface of the tongue is generated by the brightness temperature image generation component 210, and the lower surface image of the tongue 300 can be acquired by the image acquisition component 100.

In the present disclosure, as shown in FIG. 1, the connector 430 may be a short bar whose axis is horizontally disposed, and the support portion 410 may be a rod disposed vertically.

According to an embodiment of the present disclosure, at least one of the image acquisition component 100 and the temperature acquisition component 200 may be moved on the mounting portion 420 such that the distance between the image acquisition component 100 and the temperature acquisition component 200 may be changed.

As another embodiment of the present disclosure, the support portion 410 extends in a predetermined direction. Specifically, when the tongue manifestation detecting apparatus is in the operating state shown in FIG. 1, the predetermined direction is a vertical direction. That is, the support portion 410 has a certain height. The connector 430 and the mounting portion 420 can be reciprocally moved in the predetermined direction (i.e., the vertical direction in FIG. 1) of the support portion 410. For example, the support portion 410 may be a ball screw, and the connector 430 may be provided on the nut of the ball screw. The ball screw is driven by the servo motor to rotate so that the nut can be reciprocated along the axis of the ball screw and the connector 430 is driven to reciprocate along the axis of the ball screw.

The connector 430 may be fixedly connected to the support portion 410 at one end and may be rotatably connected to the mounting portion 420 at the other end. Alternatively, the connector 430 may be rotatably connected to the support portion 410 at one end and may be fixedly connected to the mounting portion 420 at the other end.

In order to facilitate the acquisition of the tongue manifestation, preferably, as shown in FIG. 1, the mounting portion 420 is a curved beam, and the connector 430 is provided on a middle portion of the mounting portion 420. In this way, the subject's tongue can be held between the image acquisition component 100 and the temperature acquisition component 200.

As described above, the distance between the image acquisition component 100 and the temperature acquisition component 200 can be adjusted, and accordingly, a guide rail may be formed on the mounting portion 420, and a slider may be provided on the image acquisition component 100 or the temperature acquisition component 200. The slider is movable along the guide rail, and the slider can also be fixed to the mounting portion 420.

In order to facilitate the installation and placement of the tongue manifestation detecting apparatus, preferably, the tongue manifestation detecting apparatus further comprises a base 500 on which the mounting bracket 400 is fixed.

It is to be understood that the above embodiments are merely illustrative embodiments for the purpose of illustrating the principles of the present disclosure. However, the present disclosure is not limited thereto. It will be apparent to those skilled in the art that various modifications and improvements can be made therein without departing from the spirit and substance of the present disclosure. Accordingly, all of the modifications and improvements also fall into the protection scope of the present disclosure.

The invention claimed is:
1. A tongue manifestation detecting device, comprising:
 an image acquisition component configured to acquire a surface image of a tongue;
 a temperature acquisition component configured to acquire parameters characterized by the temperature of the tongue; and a brightness temperature image generation component configured to generate a brightness temperature image of the tongue based on the parameters characterized by the temperature of the tongue acquired by the temperature acquisition component;

wherein the image acquisition component comprises a light source, a spectroscope, a filter lens, a controllable lens and an imaging component;

the focal length of the controllable lens is adjustable;

the imaging component is provided in the reflected light path of the spectroscope, and is configured to generate the surface image of the tongue;

the light source, the spectroscope, the filter lens and the controllable lens are arranged in the same straight line in this order, and the imaging component and the spectroscope are arranged in another straight line; and the straight line where the imaging component and the spectroscope are located is perpendicular to the straight line where the light source, the spectroscope, the filter lens and the controllable lens are located.

2. The tongue manifestation detecting device of claim 1, wherein the parameter characterized by the temperature of the tongue comprises an intensity of the infrared emitted from the tongue;

wherein the temperature acquisition component is configured to acquire an intensity value of the infrared emitted from the tongue; and wherein the brightness temperature image generation component is configured to generate the brightness temperature image of the tongue based on the intensity value of the infrared acquired by the temperature acquisition component.

3. The tongue manifestation detecting device of claim 2, wherein the temperature acquisition component stores an initial standard infrared intensity value, and is configured to calculate the intensity value of the infrared emitted from the tongue according to the following formula:

$$If_i = If_r - If_s;$$

where $If_i$ represents the intensity value of the infrared emitted from the tongue, $If_r$ represents an intensity value of the received infrared, and $If_s$ represents the initial standard infrared intensity value.

4. The tongue manifestation detecting device of claim 1, further comprising an infrared light source configured to emit infrared to the tongue, wherein the temperature acquisition component is configured to receive infrared from the tongue and is configured to calculate the intensity of the infrared emitted from the tongue based on the intensity of the infrared emitted from the infrared light source and the intensity of the infrared received from the tongue.

5. The tongue manifestation detecting device of claim 4, wherein the infrared light source comprises a plurality of infrared light-emitting diodes arranged in an array form.

6. The tongue manifestation detecting device of claim 5, wherein the plurality of infrared light-emitting diodes are configured to emit infrared with different wavelengths alternately;

wherein the temperature acquisition component is configured to acquire the intensity of the infrared reflected by the tongue when irradiated by the infrared of various wavelengths; and wherein the brightness temperature image generation component is configured to generate a plurality of brightness temperature images of the tongue based on the infrared intensity, corresponding to the plurality of the infrared light-emitting diodes, acquired by the temperature acquisition component.

7. A tongue manifestation detecting apparatus comprising the tongue manifestation detecting device including the image acquisition component, the temperature acquisition component and the brightness temperature image generation component of claim 1, further comprising a mounting bracket including a support portion, a mounting portion and a connector, wherein the connector is connected to the mounting portion at one end and is connected to the support portion at the other end such that the mounting portion is located on just one side of the support portion;

wherein the image acquisition component and the temperature acquisition component are provided on the two ends of the mounting portion, respectively; and wherein the mounting portion is configured to rotate around the connector to exchange the relative positions of the image acquisition component and the temperature acquisition component.

8. The tongue manifestation detecting apparatus of claim 7, wherein at least one of the image acquisition component and the temperature acquisition component is configured to move on the mounting portion such that the distance between the image acquisition component and the temperature acquisition component is changeable.

9. The tongue manifestation detecting apparatus of claim 7, wherein the mounting portion is a curved beam;

wherein the opening of the mounting portion faces away from the support portion; and wherein one end of the connector is connected to a middle portion of the mounting portion.

10. The tongue manifestation detecting apparatus of claim 7, wherein the support portion extends in a predetermined direction; and wherein the connector can be reciprocally moved in the predetermined direction of the support portion to drive the mounting portion to reciprocate in the predetermined direction of the support portion.

11. The tongue manifestation detecting apparatus of claim 7, further comprising a base on which the mounting bracket is fixed.

12. A tongue manifestation detecting device, comprising:

an image acquisition component configured to acquire a surface image of a tongue;

a temperature acquisition component configured to acquire parameters characterized by the temperature of the tongue; and a brightness temperature image generation component configured to generate a brightness temperature image of the tongue based on the parameters characterized by the temperature of the tongue acquired by the temperature acquisition component;

wherein the image acquisition component comprises a light source, a spectroscope, a filter lens, a controllable lens and an imaging component;

the focal length of the controllable lens is adjustable;

the imaging component is provided in the reflected light path of the spectroscope, and is configured to generate the surface image of the tongue;

the light source, the spectroscope the filter lens and the controllable lens are arranged in the same straight line in this order, and the imaging component and the spectroscope are arranged in another straight line; and the straight line where the imaging component and the spectroscope are located is perpendicular to the straight line where the light source, the spectroscope, the filter lens and the controllable lens are located;

wherein the image acquisition component further comprises an image delayer and a controllable grating both provided between the imaging component and the spectroscope;

the imaging component comprises an image sensor and a mirror;

the mirror, the image delayer, the controllable grating and the spectroscope are arranged in the same straight line in this order;

the reflecting surface of the mirror faces a light outlet of the image delayer, and there is an angle between the reflecting surface of the mirror and the straight line where the mirror, the image delayer, the controllable grating and the spectroscope are located; and the light passing through the image delayer is reflected by the mirror to the image sensor.

13. A tongue manifestation detecting apparatus comprising the tongue manifestation detecting device including the image acquisition component, the temperature acquisition component and the brightness temperature image generation component of claim 12, further comprising a mounting bracket including a support portion, a mounting portion and a connector, wherein the connector is connected to the mounting portion at one end and is connected to the support portion at the other end such that the mounting portion is located on just one side of the support portion;

wherein the image acquisition component and the temperature acquisition component are provided on the two ends of the mounting portion, respectively; and wherein the mounting portion is configured to rotate around the connector to exchange the relative positions of the image acquisition component and the temperature acquisition component.

14. The tongue manifestation detecting apparatus of claim 13, wherein at least one of the image acquisition component and the temperature acquisition component is configured to move on the mounting portion such that the distance between the image acquisition component and the temperature acquisition component is changeable.

15. The tongue manifestation detecting apparatus of claim 13, wherein the mounting portion is a curved beam;

wherein the opening of the mounting portion faces away from the support portion; and wherein one end of the connector is connected to a middle portion of the mounting portion.

16. The tongue manifestation detecting apparatus of claim 13, wherein the support portion extends in a predetermined direction; and wherein the connector can be reciprocally moved in the predetermined direction of the support portion to drive the mounting portion to reciprocate in the predetermined direction of the support portion.

17. The tongue manifestation detecting apparatus of claim 13, further comprising a base on which the mounting bracket is fixed.

* * * * *